(12) United States Patent  
Martinez et al.

(10) Patent No.: US 11,571,271 B2  
(45) Date of Patent: Feb. 7, 2023

(54) TISSUE EXPANDERS AND METHODS OF USE THEREOF

(71) Applicant: Establishment Labs S.A., Alajuela (CR)

(72) Inventors: Nicole Martinez, Alajuela (CR); Nathalia Araujo, Alajuela (CR); Roberto De Mezerville, Alajuela (CR); Juan José Chacón Quirós, Alajuela (CR)

(73) Assignee: Establishment Labs S.A., Alajuela (CR)

( * ) Notice: Subject to any disclaimer, the term of this patent is extended or adjusted under 35 U.S.C. 154(b) by 273 days.

(21) Appl. No.: 16/345,261

(22) PCT Filed: Oct. 27, 2017

(86) PCT No.: PCT/IB2017/001449  
§ 371 (c)(1),  
(2) Date: Apr. 26, 2019

(87) PCT Pub. No.: WO2018/078446  
PCT Pub. Date: May 3, 2018

(65) Prior Publication Data  
US 2019/0290382 A1    Sep. 26, 2019

Related U.S. Application Data

(60) Provisional application No. 62/414,269, filed on Oct. 28, 2016.

(51) Int. Cl.  
*A61B 90/00* (2016.01)  
*A61F 2/12* (2006.01)  
(Continued)

(52) U.S. Cl.  
CPC .............. *A61B 90/02* (2016.02); *A61F 2/12* (2013.01); *A61B 17/12022* (2013.01);  
(Continued)

(58) Field of Classification Search  
CPC .............. A61B 90/02; A61B 17/22032; A61B 17/12022; A61B 2017/22051;  
(Continued)

(56) References Cited

U.S. PATENT DOCUMENTS

| 4,574,780 A | 3/1986 | Manders |
| 4,671,255 A | 6/1987 | Dubrul et al. |

(Continued)

FOREIGN PATENT DOCUMENTS

| BR | 112019007293 A2 | 7/2019 |
| CA | 3041435 A1 | 5/2018 |

(Continued)

OTHER PUBLICATIONS

International Search Report for Application No. PCT/IB2017/001449, dated Mar. 26, 2018 (3 pages).

(Continued)

*Primary Examiner* — Richard G Louis  
*Assistant Examiner* — Chima U Igboko  
(74) *Attorney, Agent, or Firm* — Schwegman Lundberg & Woessner, P.A.

(57) ABSTRACT

Tissue expanders and methods of their manufacture and use are disclosed herein. A tissue expander shell according to the present disclosure may include a shape and topography that facilitates uniform or substantially uniform expansion and contraction of the tissue expander. In at least one example, the shell may include a series of topographical features, such as ridges, grooves, channels, valleys, canals, protrusions, pleats, creases, or folds. In some embodiments, these features may have a curved or wavy cross sectional profile. For (Continued)

example, the shell may include a series of concentric curved ridges.

17 Claims, 5 Drawing Sheets

(51) Int. Cl.
| | |
|---|---|
| A61B 17/00 | (2006.01) |
| A61B 17/22 | (2006.01) |
| A61M 25/10 | (2013.01) |
| A61F 2/00 | (2006.01) |
| A61M 29/02 | (2006.01) |
| A61F 5/00 | (2006.01) |
| A61B 17/12 | (2006.01) |

(52) U.S. Cl.
CPC ............... *A61B 17/22032* (2013.01); *A61B 2017/00526* (2013.01); *A61B 2017/00557* (2013.01); *A61B 2017/22051* (2013.01); *A61F 2/0013* (2013.01); *A61F 5/003* (2013.01); *A61M 25/10* (2013.01); *A61M 29/02* (2013.01)

(58) Field of Classification Search
CPC .......... A61B 2017/00526; A61B 2017/00557; A61B 2017/00792; A61B 2017/00796; A61F 2/12; A61F 2/0013; A61F 5/003; A61F 2210/0061; A61M 25/10; A61M 29/02

See application file for complete search history.

(56) References Cited

U.S. PATENT DOCUMENTS

| | | | |
|---|---|---|---|
| 4,950,292 | A | 8/1990 | Audretsch |
| 4,955,907 | A | 9/1990 | Ledergerber |
| 5,146,933 | A | 9/1992 | Boyd |
| 5,171,269 | A | 12/1992 | Bark |
| 5,282,856 | A * | 2/1994 | Ledergerber ............ A61F 2/12 623/8 |
| 5,871,497 | A | 2/1999 | Young |
| 5,913,871 | A | 6/1999 | Werneth et al. |
| 5,935,164 | A | 8/1999 | Iversen |
| 5,977,431 | A | 11/1999 | Knapp et al. |
| 6,071,309 | A | 6/2000 | Knowlton |
| 6,228,116 | B1 | 5/2001 | Ledergerber |
| 6,588,432 | B1 | 7/2003 | Rehder et al. |
| 6,605,116 | B2 | 8/2003 | Falcon et al. |
| 6,743,254 | B2 | 6/2004 | Guest et al. |
| 6,875,233 | B1 | 4/2005 | Turner |
| 7,081,136 | B1 | 7/2006 | Becker |
| 7,575,597 | B2 | 8/2009 | Rehnke |
| D604,849 | S | 11/2009 | Lauryssen |
| D605,767 | S | 12/2009 | Lauryssen |
| 7,731,700 | B1 | 6/2010 | Schytte |
| 8,167,836 | B2 | 5/2012 | Lee et al. |
| 8,192,486 | B2 | 6/2012 | Glicksman |
| 8,398,710 | B2 | 3/2013 | Forsell |
| 8,454,690 | B2 | 6/2013 | McClellan |
| 8,506,627 | B2 | 8/2013 | Van Epps et al. |
| 8,636,797 | B2 | 1/2014 | Chitre et al. |
| 8,821,574 | B2 | 9/2014 | Davodian |
| 8,852,276 | B2 | 10/2014 | Del Vecchio |
| 8,870,952 | B2 | 10/2014 | Holland et al. |
| 9,017,403 | B2 | 4/2015 | Forsell |
| 9,138,311 | B2 | 9/2015 | Van Epps et al. |
| 9,393,106 | B2 | 7/2016 | Van Epps et al. |
| 9,399,122 | B2 | 7/2016 | Mosharrafa et al. |
| 9,463,087 | B2 | 10/2016 | Hristov et al. |
| 9,526,584 | B2 | 12/2016 | Payne et al. |
| 9,549,812 | B2 | 1/2017 | Shetty et al. |
| 9,636,210 | B2 | 5/2017 | Hristov et al. |
| 9,700,404 | B2 | 7/2017 | Martin et al. |
| 9,700,405 | B2 | 7/2017 | Davila et al. |
| 9,724,189 | B2 | 8/2017 | Forsell |
| 9,808,338 | B2 | 11/2017 | Schuessler et al. |
| 9,814,566 | B1 | 11/2017 | Cree |
| 9,918,829 | B2 | 3/2018 | Van Epps et al. |
| 10,004,590 | B2 | 6/2018 | Shetty et al. |
| 10,010,404 | B2 | 7/2018 | McClellan |
| 10,052,190 | B2 | 8/2018 | Chitre et al. |
| 10,245,117 | B2 | 4/2019 | Payne et al. |
| 10,251,746 | B2 | 4/2019 | Schuessler et al. |
| 10,537,420 | B2 | 1/2020 | Forsell |
| 10,588,737 | B2 | 3/2020 | McClellan |
| 10,617,516 | B2 | 4/2020 | Davila et al. |
| D616,096 | S | 5/2020 | Lauryssen |
| 10,660,742 | B2 | 5/2020 | Algawi et al. |
| 10,695,165 | B2 | 6/2020 | Shetty et al. |
| D889,654 | S | 7/2020 | Limem et al. |
| D889,655 | S | 7/2020 | Limem et al. |
| 10,709,851 | B2 | 7/2020 | Geiger |
| D892,329 | S | 8/2020 | Limem et al. |
| 10,751,162 | B2 | 8/2020 | Hristov et al. |
| 10,751,163 | B2 | 8/2020 | Feinberg et al. |
| 10,751,164 | B2 | 8/2020 | Govari et al. |
| D896,383 | S | 9/2020 | Schuessler et al. |
| 10,765,506 | B2 | 9/2020 | Chitre et al. |
| 10,792,121 | B2 | 10/2020 | Jones et al. |
| 10,799,313 | B2 | 10/2020 | Davila et al. |
| 10,799,337 | B2 | 10/2020 | David et al. |
| 10,820,984 | B2 | 11/2020 | Renke |
| 10,828,148 | B2 | 11/2020 | Forsell |
| 10,898,313 | B2 | 1/2021 | Feinberg et al. |
| 11,039,898 | B2 | 6/2021 | McClellan |
| 11,065,075 | B2 | 7/2021 | Mosharrafa |
| D926,984 | S | 8/2021 | Schuessler et al. |
| D927,690 | S | 8/2021 | Limem et al. |
| 11,154,393 | B2 | 10/2021 | Limem et al. |
| 11,160,630 | B2 | 11/2021 | Schuessler et al. |
| 11,207,149 | B2 | 12/2021 | McClellan |
| 2001/0004709 | A1 | 6/2001 | Dubrul |
| 2002/0038147 | A1 | 3/2002 | Miller, III |
| 2003/0144734 | A1 | 7/2003 | Dreschnack et al. |
| 2007/0227428 | A1* | 10/2007 | Brennan ............ B81C 1/00206 114/67 R |
| 2008/0188923 | A1* | 8/2008 | Chu ................ A61B 17/12118 623/1.15 |
| 2009/0281612 | A1 | 11/2009 | Johnson |
| 2010/0042211 | A1 | 2/2010 | Van Epps et al. |
| 2011/0152683 | A1 | 6/2011 | Gerrans et al. |
| 2012/0259428 | A1* | 10/2012 | Brogan ................ A61F 2/0059 623/23.72 |
| 2013/0325120 | A1 | 12/2013 | McClellan |
| 2014/0074237 | A1 | 3/2014 | Yacoub et al. |
| 2014/0336507 | A1 | 11/2014 | Cheng |
| 2015/0245902 | A1* | 9/2015 | Becker ................. A61F 2/12 623/8 |
| 2015/0245903 | A1 | 9/2015 | Becker |
| 2015/0351900 | A1 | 12/2015 | Glicksman |
| 2017/0014226 | A1 | 1/2017 | Fenaroli |
| 2017/0348089 | A1 | 12/2017 | Becker |
| 2018/0110612 | A1 | 4/2018 | Schuessler et al. |
| 2019/0223971 | A1 | 7/2019 | Payne et al. |
| 2019/0247138 | A1 | 8/2019 | Kirchhevel et al. |
| 2020/0100892 | A1 | 4/2020 | Limem et al. |
| 2020/0146811 | A1 | 5/2020 | Forsell |
| 2020/0246132 | A1 | 8/2020 | Scott |
| 2020/0253717 | A1 | 8/2020 | Nygaard |
| 2020/0268504 | A1 | 8/2020 | Chitre et al. |
| 2020/0276397 | A1 | 9/2020 | Geiger |
| 2020/0281714 | A1 | 9/2020 | Shetty et al. |
| 2020/0297479 | A1 | 9/2020 | Van Epps et al. |
| 2020/0315777 | A1 | 10/2020 | Becker |
| 2020/0352704 | A1 | 11/2020 | Schuessler et al. |
| 2020/0383773 | A1 | 12/2020 | Feinberg et al. |
| 2020/0405473 | A1 | 12/2020 | Nanni et al. |
| 2021/0093444 | A1 | 4/2021 | Feinberg et al. |
| 2021/0121284 | A1 | 4/2021 | Forsell |
| 2021/0259798 | A1 | 8/2021 | Jones et al. |

(56) References Cited

U.S. PATENT DOCUMENTS

| | | |
|---|---|---|
| 2021/0307858 A1 | 10/2021 | McClellan |
| 2021/0346112 A1 | 11/2021 | Mosharrafa |

FOREIGN PATENT DOCUMENTS

| | | |
|---|---|---|
| CN | 10984321 A | 6/2019 |
| EP | 3531956 A1 | 9/2019 |
| HK | 40014051 A | 8/2020 |
| IL | 265954 | 5/2019 |
| KR | 20150138164 | 12/2015 |
| KR | 20190075940 A | 7/2019 |
| WO | 9526696 | 10/1995 |
| WO | 2009126507 A2 | 10/2009 |
| WO | WO 2014/118773 A1 | 8/2014 |
| WO | WO 2014/168926 A1 | 10/2014 |
| WO | WO-2015153065 A1 | 10/2015 |
| WO | WO 2016/005667 A1 | 1/2016 |
| WO | WO-2018078446 A1 | 5/2018 |
| WO | WO 2019/110550 A1 | 6/2019 |
| WO | WO 2019/245241 A1 | 12/2019 |
| WO | WO 2021/045570 A2 | 3/2021 |
| WO | WO 2021/066472 A1 | 4/2021 |
| WO | WO 2021/217099 A1 | 10/2021 |

OTHER PUBLICATIONS

"Chinese Application Serial No. 201780063706.4, Office Action dated Jun. 29, 2022", w o English translation, 4 pgs.

"Chinese Application Serial No. 201780063706.4, Response filed May 16, 2022 to Office Action dated Nov. 1, 2021", w English claims, 15 pgs.

"Israel Application Serial No. 265954, Response filed May 30, 2022 to Office Action dated Dec. 14, 2021", w English claims, 15 pgs.

"Israel Application Serial No. 265954, Office Action dated Jul. 20, 2022", w English translation, 4 pgs.

"Brazilian Application Serial No. 112019007293-4, Office Action dated Jan. 24, 2022", w/ English Translation, 5 pgs.

"Brazilian Application Serial No. 112019007293-4, Response filed May 13, 2022 to Office Action dated Jan. 24, 2022", w/ English claims, 55 pgs.

"Chinese Application Serial No. 201780063706.4, Office Action dated Nov. 1, 2021", w/English translation, 18 pgs.

"European Application Serial No. 17818254.9, Response to Communication pursuant to Rules 161(1) and 162 EPC filed Jan. 2, 2020", 12 pgs.

"International Application Serial No. PCT/IB2017/001449, International Preliminary Report on Patentability dated May 9, 2019", 11 pgs.

"International Application Serial No. PCT/IB2017/001449, Written Opinion dated Mar. 26, 2018", 9 pgs.

"Israel Application Serial No. 265954, Office Action dated Dec. 14, 2021", 3 pgs.

"Korean Application Serial No. 10-2019-7012393, Notice of Preliminary Rejection dated Jan. 21, 2022", w/ English Translation, 17 pgs.

"Korean Application Serial No. 10-2019-7012393,Response filed Jun. 14, 2022 Preliminary Rejection dated Jan. 21, 2022", w/ English Claims, 19 pgs.

"European Application Serial No. 17818254.9, Communication Pursuant to Article 94(3) EPC dated Oct. 10, 2022", 7 pgs.

"Brazilian Application Serial No. BR112019007293-4, Office Action dated Dec. 2, 2022", W English Translation, 3 pgs.

\* cited by examiner

TISSUE EXPANDERS AND METHODS OF USE THEREOF

CROSS-REFERENCE TO RELATED APPLICATIONS

This application is the U.S. national stage entry under 35 U.S.C. § 371 of International Application No. PCT/IB2017/001449, filed on Oct. 27, 2017, which claims priority to U.S. Provisional Application No. 62/414,269, filed on Oct. 28, 2016, each of which is incorporated by reference herein in its entirety.

TECHNICAL FIELD

The present disclosure relates generally to implantable medical devices such as tissue expanders and methods of use thereof.

BACKGROUND

Patients have implants for a variety of medical and/or esthetic reasons. Implants may be useful to correct natural asymmetries in body shape, to adjust the size and/or shape of certain features, or for post-operative reconstruction. For example, a breast prosthesis may be used to augment or decrease the size of the breast, or to correct asymmetry in breast shape or volume following surgery, such as a mastectomy or partial mastectomy to remove cancerous breast tissue. Prior to implantation of a prosthesis, a sizer or tissue expander may be inserted temporarily to help to create or maintain the space necessary for the more permanent prosthesis. Keeping living tissues under tension by means of a tissue expander can promote formation of new tissue. As the tissue expander is enlarged over time, the surrounding tissues can expand to the point where the prosthesis may be implanted. Tissue expanders also may be used to spur the growth of new skin and subcutaneous tissue in other parts of the body.

BRIEF DESCRIPTION OF THE DRAWINGS

The accompanying drawings, which are incorporated in and constitute a part of this specification, illustrate various examples and, together with the description, serve to explain the principles of the present disclosure. Any features of an embodiment or example described herein (e.g., device, method, etc.) may be combined with any other embodiment or example, and such combinations are encompassed by the present disclosure.

SUMMARY

Figure 1A:
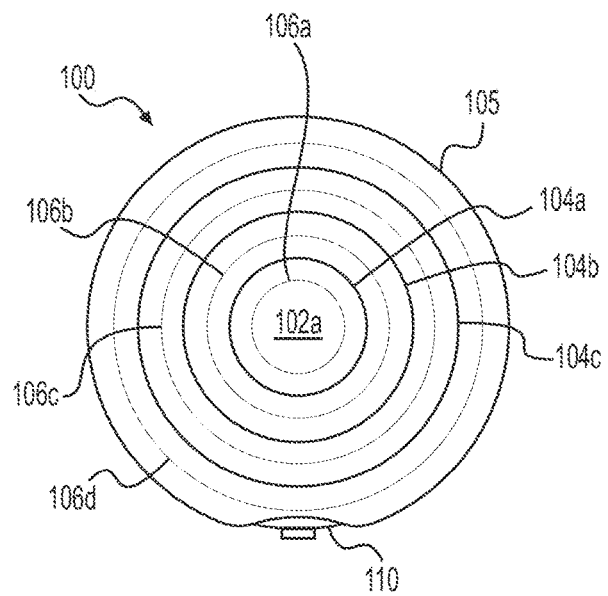
FIGS. 1A and 1B show an exemplary device, according to some aspects of the present disclosure.

Aspects of the present disclosure include a tissue expander having a flexible shell. The shell defines a cavity therein, and includes a plurality of ridges that curve along a surface of the shell about an axis, each ridge having a width and a length longer than the width. In some embodiments, the shell includes an anterior side and a posterior side, the anterior side having an apex, wherein each ridge of the plurality of ridges is disposed circumferentially around the apex. In further embodiments, the plurality of ridges includes a first annular ridge and a second annular ridge concentric with the first annular ridge.

In yet further embodiments, the plurality of curved ridges includes at least one channel connecting two adjacent ridges. In some such embodiments, the at least one channel includes two channels each extending radially outward, the two channels being disposed at least 45° apart about a circumference of the shell.

In still further embodiments, the plurality of ridges includes a first ridge and a second ridge, the shell further including a plurality of channels connecting the first ridge and the second ridge, wherein the plurality of channels are circumferentially disposed at intervals around an apex of the shell. In further embodiments, the plurality of ridges includes at least three ridges each separated from an adjacent ridge by a valley. In some such embodiments, the at least three ridges are disposed circumferentially around an apex of the shell, and the plurality of channels comprises: a first channel connecting the first ridge to the second ridge and traversing the valley between them; and a second channel connecting the second ridge to the third ridge and traversing the valley between them. In some such embodiments, the first channel, the second channel, and the apex are not co-linear. In some such embodiments, the first channel does not connect to the third ridge.

In some embodiments, the shell of the tissue expander is flexible and comprises silicone, polyurethane, or a copolymer thereof. In some embodiments, the shell has a uniform thickness ranging from about 0.3 mm to about 0.6 mm. In further embodiments, at least one of the anterior side or the posterior side of the shell is textured. In further embodiments, the tissue expander includes a port connector coupled to the shell.

Aspects of the present disclosure also include a tissue expander including a flexible shell defining a cavity therein. The shell includes a plurality of ridges, each ridge curving along a surface of the shell around an apex, and each ridge having a width and a length longer than the width. The shell also includes a channel connecting at least two of the ridges, and the shell has a uniform thickness.

In some such embodiments, the channel is a first channel, and the shell further includes a second channel connecting at least two of the ridges. In further embodiments, the plurality of ridges includes at least three concentric ridges. In yet further embodiments, the shell includes a plurality of channels, each channel connecting only two adjacent ridges of the plurality of ridges. In some embodiments, the tissue expander includes a port connector integrated into a portion of the shell.

Aspects of the present disclosure also include a tissue expander having a flexible shell defining a cavity therein, where the shell includes a plurality of parallel ridges that curve along a surface of the shell, each ridge having a width and a length longer than the width, and a plurality of channels extending radially outward, each channel connecting at least two adjacent ridges of the plurality of ridges.

In some such embodiments, the plurality of channels are disposed in a staggered configuration. In further embodiments, the tissue expander has a circular, oval, rectangular, spherical, crescent, or teardrop cross-sectional shape. In yet further embodiments, the plurality of parallel ridges comprises concentric ridges on an anterior surface of the shell, and the shell is configured to distribute force applied to the anterior surface radially outward. In further embodiments, the plurality of channels comprises at least three channels arranged into rows and spaced at regular intervals.

Aspects of the present disclosure also include a method of making a tissue expander. The method includes coating a mold with a liquid dispersion to form a shell, the mold including a plurality of circumferential grooves, curing the shell, and removing the shell from the mold, wherein the shell includes a plurality of ridges corresponding to the plurality of circumferential grooves of the mold.

In some embodiments, the liquid dispersion comprises silicone, polyurethane, or a mixture thereof. In further embodiments, the method further includes inverting the shell such that the plurality of ridges are disposed on an outermost surface of the shell. In further embodiments, the shell has a uniform thickness ranging from about 0.3 mm to about 0.6 mm.

Aspects of the present disclosure also include a tissue expander mold. The tissue expander mold includes: a body including a plurality of circumferential grooves, each groove curving along a surface of the body about a center axis of the body, each groove having a width and a length longer than the width; and a depression connecting at least two of the grooves.

In some embodiments, the plurality of grooves includes at least three grooves that curve parallel to each other around an apex of the body. In further embodiments, the surface of the body is texturized.

DETAILED DESCRIPTION

Particular aspects of the present disclosure are described in greater detail below. The terms and definitions provided herein control, if in conflict with terms and/or definitions incorporated by reference.

As used herein, the terms "comprises," "comprising," or any other variation thereof are intended to cover a non-exclusive inclusion, such that a process, method, composition, article, or apparatus that comprises a list of elements does not include only those elements, but may include other elements not expressly listed or inherent to such process, method, composition, article, or apparatus. The term "exemplary" is used in the sense of "example" rather than "ideal."

As used herein, the singular forms "a," "an," and "the" include plural reference unless the context dictates otherwise. The terms "approximately" and "about" refer to being nearly the same as a referenced number or value. As used herein, the terms "approximately" and "about" should be understood to encompass±10% of a specified amount or value.

As used herein, the term "posterior" refers to the back of a patient, and the term "anterior" refers to front of a patient. Thus, the posterior side of a breast implant is the side of the implant facing the chest wall, while the anterior side is the opposite side closest to the skin. Similarly, the posterior side of a gluteal or buttock implant is the side closest to the skin, and the anterior side is the opposite side facing the pelvis.

Tissue expanders may be used to stretch or promote growth of tissue in a patient in preparation for an implant. For example, a surgeon may place a tissue expander in a mastectomy patient as part of reconstructive repair of breast tissue. Tissue expanders generally include a fill port to allow for introduction of a liquid or gel (e.g., saline solution or other biocompatible liquid or gel) over time. The prosthesis is typically implanted into the breast cavity in an empty or only partially filled state. The implant may then be inflated to its desired size via a valve or fill port. Gradual inflation at pre-determined intervals may cause the skin and subcutaneous tissues overlying the expander to expand in response to the pressure exerted upon the tissue as the liquid or gel is introduced into the tissue expander. The skin and subcutaneous tissue may expand to the point where further medical procedures can be performed, such as the permanent implantation of a prosthesis, plastic and reconstructive surgery, or for use of the skin and subcutaneous tissue for use in some other part of the body.

Volume adjustment may be beneficial, e.g., to make a later adjustment of size without having to replace the prosthesis with one of a different size, which would require a subsequent surgical procedure.

Tissue expansion may occur over the span of weeks to months, e.g., from about 4 weeks to about 24 weeks, or from about 6 weeks to about 8 weeks, e.g., about 4, 6, 8, 10, 12, 14, or 16 weeks or more.

Tissue expanders (sometimes known as "sizers") according to the present disclosure may comprise a flexible shell that allows for their expansion and contraction, e.g., upon introduction and removal, respectively, of a fluid in a cavity defined by the shell. In some aspects of the present disclosure, a shell of a tissue expander may have a shape and topography that facilitates uniform or substantially uniform expansion of the tissue expander. For example, the topography of a tissue expander shell may promote an even distribution of force of fluid within the tissue expander against the inner surface of the shell as the fluid is introduced into the shell. The topography of the shell may also promote an even distribution of force of the outer surface of the tissue expander against surrounding tissue, even as the device expands and changes sizes. Additionally or alternatively, the topography of the shell may promote retention of the shell's shape, with or without fluid inside, by discouraging wrinkling or unwanted folding of the shell. Tissue expanders may be implanted in a patient for a number of weeks or months, e.g., from about 4 weeks to about 8 months, or from about 6 weeks to about 6 months, e.g., about 4, 6, 8, 10, 12, 14, 16, 20, or 24 weeks or more.

In some embodiments of the present disclosure, the shell may have an approximately uniform thickness. In alternative embodiments, the shell may have a thickness that is greater on one side than the other (e.g., a posterior side of the shell may be thicker than an anterior side of the shell), or within different areas or regions of the shell. The thickness of the shell may range from about 0.1 mm to about 1.2 mm, such as from about 0.2 mm to about 0.8 mm, from about 0.3 mm to about 1.1 mm, from about 0.3 mm to about 0.4 mm, or from about 0.4 mm to about 0.6 mm. In some examples, the thickness of the shell may range from about 0.33 mm to 1.02 mm, e.g., a thickness of about 0.35 mm, about 0.4 mm, about 0.45 mm, about 0.5 mm, about 0.6 mm, about 0.7 mm, about 0.8 mm, about 0.9 mm, or about 1.0 mm. For example, the shell may have a uniform thickness ranging from about 0.4 mm to about 0.6 mm.

In at least one example, the shell may include a series of features, such as grooves, canals, protrusions (e.g., rounded or folded ridges), pleats, creases, or folds, that allow the device to expand uniformly (e.g., similar to a bellows), promote even distribution of force of the device against surrounding tissue in which the device is implanted, and/or promote retention of the device's shape when both expanded and contracted. Thus, for example, the configuration of the shell may help to control the way forces are applied to the device and/or to accommodate changes in volume while minimizing or avoiding wrinkling, bending, or twisting of the shell. In some embodiments, these features may have a curved or wavy cross sectional profile. For example, the shell may include a series of concentric curved pleats, having an approximately sinusoidal or wavy cross-sectional profile.

FIGS. 1A-1B, 2A-2B, 3A-3B, and 4, discussed below, illustrate various examples of tissue expanders having features that provide for such expansion characteristics. While aspects of the present disclosure may be described in the context of a given type of tissue expander, such as, for example, an expander for placement in breast tissue, embodiments of the present disclosure may be, and/or may be applied to, a variety of medical procedures. Non-limiting examples include expanders prior to placement of other body contour implants such as gluteal, calf, etc., as well as to promote growth of skin or other tissue for various reconstructive or transplantation surgeries. For example, the tissue expanders herein may be used for skin regeneration, e.g., in order to replace damaged tissue, including scarred or burned tissue.

The shell may comprise a biocompatible material or combination of biocompatible materials that allow the shell to flex. The material(s) may be elastic, such that the shell may retain its integrity after expansion and/or repeated cycles of expansion and contraction. Exemplary materials suitable for the shell include, but are not limited to, elastic polymers and copolymers, such as, e.g., silicone, polyurethane, polyurethane blends, silicone/polyurethane polymers and copolymers, polyethylene terephthalate (PET), polyether block amide (PEBA, e.g., Pebax®), and polyamide 12 (e.g., Grilamid® and Vestamid®). These materials may be formed into layers, for example, and may have varying degrees of elasticity or hardness. For example, in some aspects of the present disclosure, the shell or shell material may have an elongation value between about 350% and about 900%, such as between about 400% and about 850%, between about 450% and about 850%, between about 450% and about 750%, between about 450% and about 650%, or between about 500% and about 600%, e.g., about 350%, about 400%, about 450%, about 500%, about 550%, about 600%, about 650%, about 700%, about 750%, or about 800%. Additionally or alternatively, the shell or shell material may have a hardness between about 15 and about 95 (Shore A durometer), such as between about 25 and about 35, between about 25 and about 50, between about 30 and about 60, between about 40 and about 70, between about 50 and about 80, or between about 60 and about 90, e.g., about 20, about 25, about 30, about 35, about 40, about 45, about 50, about 55, about 60, about 65, about 70, about 75, about 80, about 85, or about 90 (Shore A durometer). Any suitable fluid may be introduced and/or removed from the tissue expanders herein, such as, e.g., water, saline solution (or other biocompatible solution), silicone gel (or other biocompatible gel), or air (or other biocompatible gas, e.g., nitrogen).

In some examples, the outer and/or inner surface of the shell may be texturized. For example, the outer and/or inner surface of the shell may include any combination of surface features (e.g., roughness, skewness, kurtosis, peak height, valley depth, and/or contact point density values) that provide a surface texture or multiple surface textures as disclosed in U.S. Provisional Application No. 62/334,667 filed on May 11, 2016, and/or U.S. Provisional Application No. 62/410,121 filed on Oct. 19, 2016, each of which is incorporated by reference herein in its entirety. In at least one example, all or a portion of the outer surface of the tissue expander may have an average roughness ($S_a$) of 4.0 µm±2 µm, a skewness value of 0.6±0.4, kurtosis value of 3.5±0.5, a maximum peak height of 14 µm±2 µm, a maximum valley depth of 12 µm±2 µm, and a contact point density ranging from 20,000 peaks/cm$^2$ to 60,000 peaks/cm$^2$, such as from 45,000 peaks/cm$^2$ to 55,000 peaks/cm$^2$. Such texturization may be provided by use of a texturized mold, as is further described elsewhere herein.

Figure 1B:
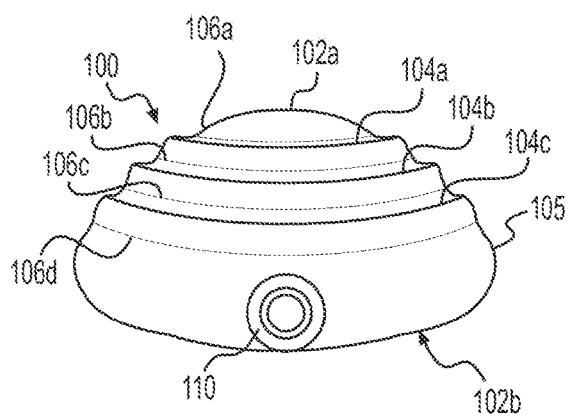

FIGS. 1A and 1B illustrate an exemplary tissue expander 100 comprising a shell 105 having an anterior side 102a and a posterior side 102b. FIG. 1A depicts a top-down view of expander 100, and FIG. 1B depicts a side view of expander 100. Expander 100 may be useful for preparing a pocket, e.g., a subglandular pocket or a submuscular pocket, in the chest tissue of a patient prior to insertion of an implant. Expander 100 may include a series of topographical features such as ridges 104a, 104b, 104c and valleys 106a, 106b, 106c on the anterior side 102a and/or the posterior side 102b, defining the surface of expander 100. The expander 100 may also include a port connection 110, which may fluidly connect the interior of expander 100 to a port, such as port 470 depicted in FIG. 4 (further discussed below). Thus, for example, shell 105 may define an expandable cavity or bladder, wherein port 470 allows for introduction and/or removal of a fluid that provides for the expansion or contraction of expander 100.

Expander 100 may have a size and shape suitable for preparing a pocket or cavity in the chest tissue of a patient for receiving a breast implant. Expander 100 may have, for example, a generally circular cross-sectional area, including a circular posterior side 102b, suitable for contacting the wall of a patient's chest cavity. The cross-sectional area may decrease from posterior side 102b to anterior side 102a, such that, upon expansion, expander 100 may have an arched or dome-like shape, similar to the shape of a breast or breast implant. Expander 100 may be expandable in the anterior-posterior direction (i.e., such that anterior side 102a moves away from posterior side 102b) upon introduction of fluid into expander 100. Likewise, expander 100 may be contractible in the anterior-posterior direction (i.e., such that anterior side 102a moves away from posterior side 102b) upon removal of fluid from within expander 100.

Ridges 104a, 104b, 104c and valleys 106a, 106b, 106c, 106d may be arranged so as to promote retention of expander 100's shape, and/or uniform expansion and contraction of expander 100. For example, as depicted in FIGS. 1A and 1B, ridges 104a, 104b, 104c may be circular or otherwise rounded (e.g., oval) ridges arranged in a concentric pattern radiating outward from a point (e.g., a center point) on anterior side 102a, and may be disposed in an alternating arrangement with circular or otherwise rounded (e.g., oval) valleys 106a, 106b, 106c between adjacent ridges and/or between a ridge and the upper or lower portion of shell 105. For example, the centermost portion of anterior side 102a may have a curved, convex shape that transitions radially outward into a valley 106a, followed by a ridge 104a, and so on. In some embodiments, ridges 104a, 104b, 104c may each have a height that is slightly greater than a depth of each of valleys 106a, 106b, 106c, 106d, such that expander 100, upon expansion, assumes a domed shape where the center of anterior side 102a is at an apex of the dome. Each ridge and valley may follow a continuous, circular path about the center of anterior side 102a, e.g., as shown in FIGS. 1A and 1B, each ridge or valley having a uniform height or depth. In other examples, one or more of the ridges and/or valleys may not be continuous about the surface of the shell, e.g., having a variable height or depth. For example, the expander may include channels and/or bridges between adjacent ridges or valleys (see, e.g., FIGS. 2A-2B, 3A-3B, and 4, discussed below).

In some embodiments, expander 100 may include more or fewer ridges and valleys than are depicted in FIGS. 1A and 1B. For example, in some embodiments, expander 100 may include two, three, five, six, seven, or more ridges and/or valleys. In some examples, the configuration of ridges and valleys may allow for each ridge to expand and/or collapse independently of the other ridges. It will be apparent to one of ordinary skill in the art that any suitable number of ridges and/or valleys may be included so as to promote uniform expansion and contraction of expander 100, promote uniform exertion of outward force by expander 100 against surrounding tissue, and/or promote retention of the shape of expander 100. In some embodiments, a suitable number of ridges and/or valleys may be included to provide structure to expander 100, such that when compressive force is applied to and/or fluid is removed from expander 100, expander 100 collapses, if at all, along the lines of the ridges and valleys, thus controlling, preventing, or reducing wrinkles in expander 100. Further, for example, the ridges may allow shell 105 to stretch in a manner so as to accommodate changes in volume without wrinkling of shell 105.

Port connection 110 may be situated in an opening in shell 105, and may be configured to fluidly connect to, e.g., a lumen or a port, through which fluid may be introduced into and/or removed from expander 100. Port connection 110 may be secured in the opening in shell 105. In some embodiments, port connection 110 may be sealed to shell 105, by, e.g., vulcanization or glue, adhered using, e.g., heat, such that fluid may not enter or exit expander 100 except for through port connection 110. In some examples, port connection 110 may comprise an integral portion of shell 105, e.g., wherein port connection 110 may be molded together with shell 105 to form a one piece component of expander 100, such that fluid enters and exits expander 100 only through port connection 110.

Figure 2A:
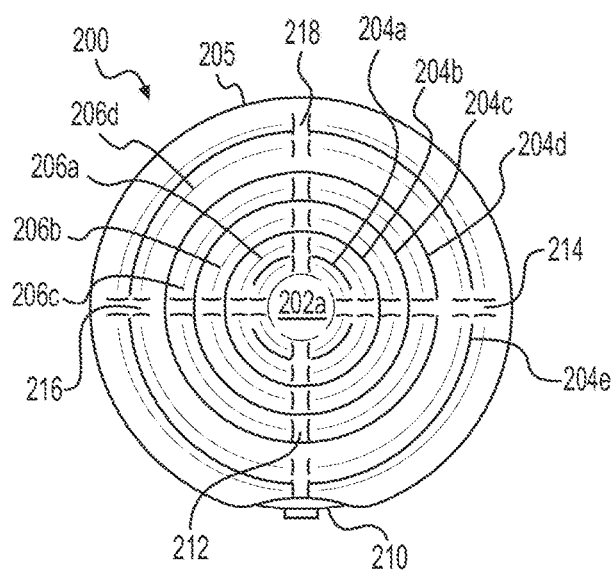
FIGS. 2A and 2B show another exemplary device, according to some aspects of the present disclosure.
Figure 2B:
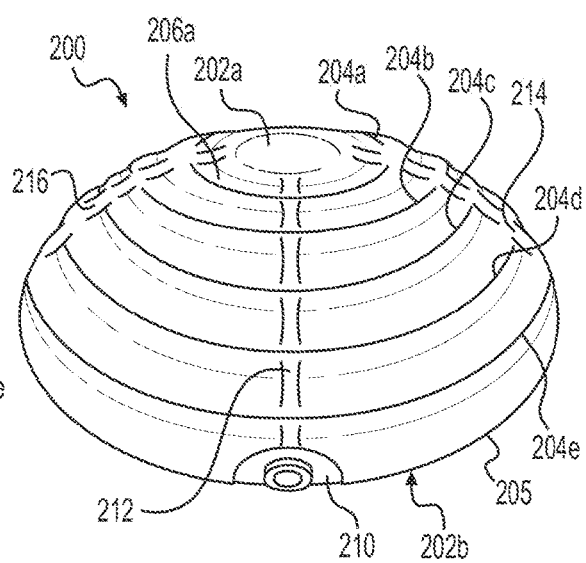

FIGS. 2A and 2B illustrate an exemplary tissue expander 200 comprising a shell 205 having an anterior side 202a and a posterior side 202b. Expander 200 may be similar to expander 100 and include any of the features of expander 100—for example, expander 200 may have a general size and shape similar to that of expander 100. Expander 200 may include ridges 204a, 204b, 204c, 204d, 204e having shapes and configurations similar to ridges 104a, 104b, 104c, as well as valleys 206a, 206b, 206c, 206d having shapes and configurations similar to valleys 106a, 106b, 106c, 106d. Expander 200 may also include a port connection 210 similar to port connection 110.

As mentioned above, the expanders herein may include features that connect ridges and/or valleys on the anterior side and/or posterior side of the shell. For example, expander 200 includes channels 212, 214, 216, 218, which may be spaced apart, and may radiate in a direction outward from a point on anterior side 202a, e.g., the center of anterior side 202a. Channels 212, 214, 216, 218 may each define a portion of shell 205 that traverses each of ridges 204a, 204b, 204c, 204d, 204e, and valleys 206a, 206b, 206c, 206d. Each channel 212, 214, 216, 218 may have a height higher than the valleys that it traverses, and equal to or lower than the ridges that it traverses. Specifically, in some examples herein, each of channels 212, 214, 216, 218 may have a height across each of valleys 206a, 206b, 206c, 206d so as to create a "break" in each valley and connect each of ridges 204a, 204b, 204c, 204d, 204e to each adjacent ridge. When viewed from the inside of shell 205, each channel may create a cavity through which fluid may flow from one ridge to another during expansion. Thus, for example, when force (e.g., compressive force) is applied to the center of anterior side 202a of expander 200, the configuration of interconnected channels and ridges may promote an even distribution of force radially outward, towards a circumference of expander 200 and toward posterior side 202b. In this manner, channels 212, 214, 216, 218 may promote the even flow of fluid between each of ridges 204a, 204b, 204c, 204d, 204e when introduced into, or removed from, expander 200. While FIGS. 2A and 2B show channels 212, 214, 216, 218 connecting all ridges 204a, 204b, 204c, 204d, 204e, in some examples, each channel may connect only a subset of the ridges, e.g., ridges 204a, 204b, and 204c; or ridges 204c, 204d, and 204e; or ridges 204a and 204b (see also FIGS. 3A-3B, discussed below). Moreover, each channel may connect a different subset of the ridges.

In some embodiments, channels 212, 214, 216, 218 may be disposed at equal intervals around a circumference of expander 200. For example, channels 212, 214, 216, 218 may be disposed at 90° intervals relative to one another, as depicted in FIGS. 2A and 2B. In further embodiments, channels 212, 214, 216, 218 may be circumferentially disposed on expander 200 at unequal intervals; for example, channel 212 and channel 214 may be disposed at, e.g., a 45° angle to one another, channel 214 and channel 218 may be disposed at a 135° angle to one another, channel 218 and channel 216 may be disposed at a 45° angle to one another, and channel 216 and channel 212 may be disposed at a 135° angle to one another. These intervals are exemplary only as channels 212, 214, 216, 218 may be disposed at generally any angles relative to each other. While four channels are depicted in FIGS. 2A and 2B, more or fewer than four channels may be present on expander 200. For example, in some embodiments, only one, two, or three of channels 212, 214, 216, 218 may be present on expander 200. In further embodiments, five, six, seven, or eight or more such channels may radiate in a direction outward on anterior surface 202a at either equal or unequal intervals. One of skill in the art will recognize that the channels may have any configuration and placement that may promote even flow of fluid inside expander 200 between each of ridges 204a, 204b, 204c, 204d, 204e, and thus a relatively even expansion of expander 200, without adversely affecting the size and shape of expander 200.

Figure 3A:
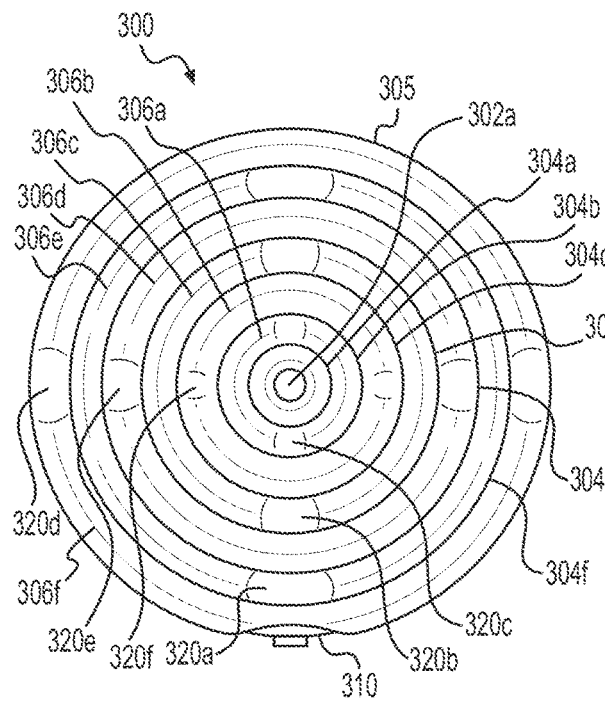
FIGS. 3A and 3B show a further exemplary device.
Figure 3B:
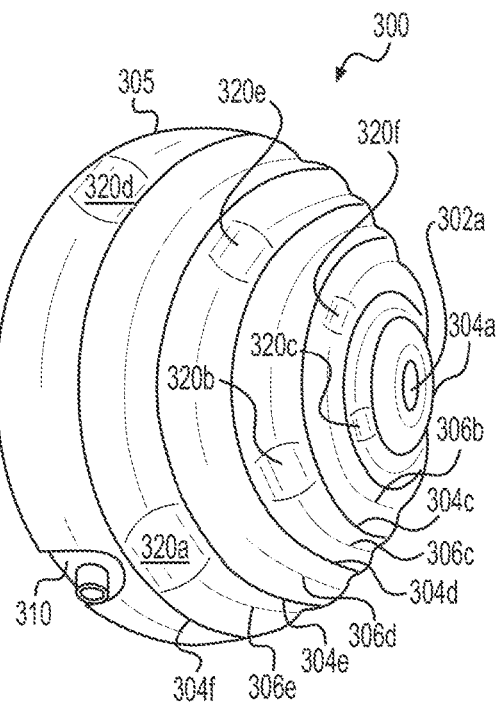

FIGS. 3A and 3B illustrate another exemplary tissue expander 300, comprising a shell 305 having an anterior side 302a and a posterior side 302b. Expander 300 may have a general configuration similar to expanders 100 and 200, and may include any features of expanders 100 and/or 200. For example, expander 300 may include ridges 304a, 304b, 304c, 304d, 304e, 304f having shapes and configurations similar to ridges 104a, 104b, 104c of expander 100, and valleys 306a, 306b, 306c, 306d, 306e, 306f having shapes and configurations similar to valleys 106a, 106b, 106c, 106d of expander 100. Expander 300 may also include a port connection 310 similar to port connection 110.

Bridges, such as bridges 320a, 320b, 320c, 320d, 320e, 320f may be disposed on anterior side 302a of expander 300 and may each constitute a short channel, e.g., a channel that connects only two ridges, or a channel that connects only a portion of the ridges, such as three adjacent ridges of a total of four or more ridges. Similar to channels 212, 214, 216, 218 of expander 200, each bridge may be a portion of the shell 305 crossing a valley between two adjacent ridges of the shell. For example, bridge 320a may be a raised portion of shell 305 crossing valley 306e, between ridges 304e and 304f. As with channels 212, 214, 216, 218, each bridge (e.g., bridges 320a, 320b, 320c, 320d, 320e, 320f) may have a height across the valley it crosses so as to create a "break" in the valley and connect each of ridges 304a, 304b, 304c, 304d, 304e, 304f to each adjacent ridge. In this manner, fluid introduced into expander 300 may travel between ridges 304a, 304b, 304c, 304d, 304e, 304f via, e.g., bridges 320a, 320b, 320c, 320d, 320e, 320f.

Bridges may have any suitable shape, such as, e.g., trapezoidal, rectangular, square, or rounded shape, among other possible shapes. Bridges may be the same size and shape as other bridges, or may have a different shape and/or size than other bridges. In some embodiments, bridges 320a, 320b, 320c, 320d, 320e, 320f may increase in size in proportion with their distance from the center of anterior side 302a. For example, bridge 320d may be proportionally larger than bridge 320f, bridge 320a may be larger than bridge 320c, and so forth. In some embodiments, bridges 320a, 320b, 320c, 320d, 320e, 320f may have a generally trapezoidal shape, such that the side of each bridge close to the outermost circumference of expander 200 is larger than the side of each bridge closer to the center of anterior side 302a. In some embodiments, the acute angles of trapezoidal bridges 320a, 320b, 320c, 320d, 320e, 320f may range from about 1° to about 44° or from about 5° to about 30°, e.g., a 15°, 20°, 25°, or 30° angle as measured from a center point of anterior side 302a.

Two or more bridges may be arranged in a row radiating outward from a point on anterior side 302a, such as a center point of anterior side 302a. Bridges in a single row may cross alternating valleys to connect adjacent pairs of ridges, e.g., without creating longer channels that extend across multiple valleys. In some embodiments, bridges in adjacent rows may cross different alternating valleys; for example, the row of bridges 320a, 320b, and 320c may cross valleys 306e, 306c, and 306a, respectively, while the adjacent row of bridges 320d, 320e, and 320f may cross valleys 306f, 306d, and 306b, respectively. In further embodiments, bridges in adjacent rows may cross the same valleys as one another. Adjacent rows of bridges may radiate outward on anterior side 302a at intervals of 180° or less, such as 60°, 90° or 120°. In some embodiments, each row of bridges radiating outward from a point on anterior side 302a may be disposed at a 180° angle or a 120° angle relative to another row of bridges having the same configuration.

Thus, for example, tissue expanders according to the present disclosure may comprise a plurality of bridges arranged in rows that are spaced at regular intervals from adjacent rows, e.g., two rows spaced 180° apart, three rows spaced 120° apart, four rows spaced 90° apart, six rows spaced 60° apart, etc. The rows need not be equally spaced apart however. Further, rows may comprise bridges at the same or a different radius (relative to the center of the anterior side) than other rows. For example, adjacent rows may comprise bridges that are located at the same radial position (see, e.g., FIGS. 2A-2B) or at different radial positions (see, e.g., FIGS. 3A-3B).

As with channels 212, 214, 216, 218 of expander 200, bridges (e.g., bridges 320a, 320b, 320c, 320d, 320e, 320f) of expander 300 may be present in a variety of numbers and configurations. For example, as depicted in FIGS. 3A and 3B, four rows of bridges may radiate outward from anterior side 302a, and the rows may be disposed about anterior side 302a at equal intervals. In further embodiments, two, three, five, six, or more rows of bridges may radiate in a direction radially outward on anterior side 302a, and may be disposed about anterior side 302a at equal or unequal intervals. For example, in one alternative configuration, a first pair of adjacent rows of bridges may be disposed at a 45° angle relative to one another, and a second pair of adjacent rows of bridges may be disposed at a 135° angle relative to one another. While FIGS. 3A and 3B depict rows of three bridges, in some examples the rows may include only two bridges, or four or more bridges. Further, different rows may include the same number of bridges, or different numbers of bridges.

In yet further embodiments, each row of bridges may include bridges crossing every third valley or every fourth valley, as opposed to every other valley. In yet further embodiments, the bridges may not be arranged in rows, but rather may be circumferentially distributed about anterior side 302a in a staggered formation. One of skill in the art will recognize that the bridges may be present in any number, configuration and placement that provides a structure that promotes even flow of fluid inside expander 300 between each of ridges 304a, 304b, 304c, 304d, 304e, 304f, without adversely affecting the size and shape of expander 300. One of skill in the art will further understand that the promotion of even flow of fluid inside expander 300 may promote even expansion of expander 300 upon introduction of fluid inside expander 300, and may prevent undesirable wrinkling of shell 300.

Similar to expander 200 above, the configuration of ridges, valleys, and channels may promote an even distribution of force. For example, when force is applied to the center of anterior side 302a, the configuration of interconnected channels and ridges may promote an even distribution of force radially outward, e.g., in a spiral. The bridges may function similar to a ladder, such that force travels to the proximate bridge and radially outward from an inner ridge to an adjacent outer ridge, then along the outer ridge until it encounters the next bridge, and so on. This distribution of force generated on the anterior side 302a of shell 305 (both inside and outside shell 305) may provide for greater control over changes in volume and a more uniform expansion. Thus, for example, a concentric pattern of interconnected ridges and valleys may allow shell 305 to stretch in order to accommodate changes in volume while avoiding, preventing, or reducing wrinkling of shell 305.

Figure 3C:
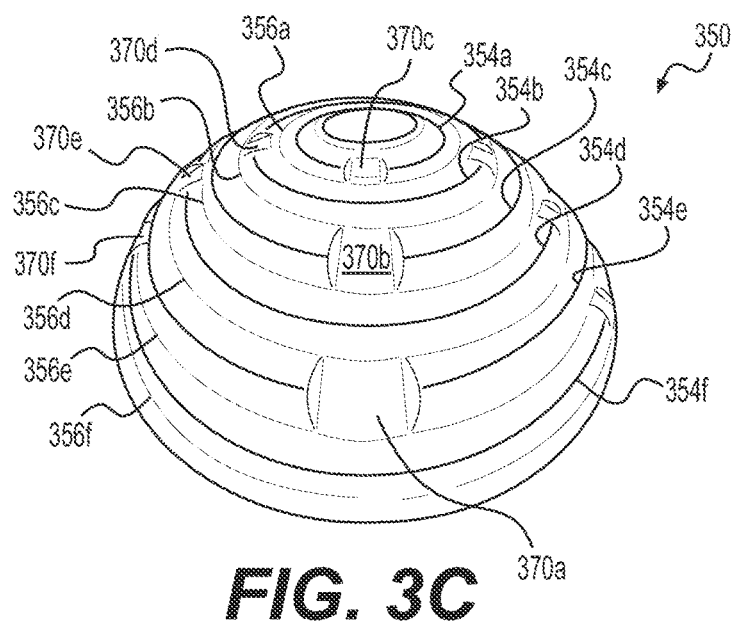
FIG. 3C shows a mold for the device, according to some aspects of the present disclosure.

FIG. 3C depicts an exemplary mold 350, which may be used to prepare an expander, such as expander 300. Mold 350 may have a general shape and size corresponding to a desired shape and size of expander 300. Mold 350 may have an upper surface 352a and a lower surface 352b. Additionally, mold 350 may have a surface topography which is the inverse (mirror image) of a desired topography of expander 300. For example, mold 350 may have circumferential grooves 354a, 354b, 354c, 354d, 354e, 354f (corresponding to ridges 304a, 304b, 304c, 304d, 304e, 304f of expander 300) separated by hills 356a, 356b, 356c, 356d, 356e, 356f (corresponding to valleys 306a, 306b, 306c, 306d, 306e, 306f of expander 300). Additionally, mold 350 may have a plurality of depressions, e.g., depressions 370a, 370b, 370c, 370d, 370e, 370f crossing hills 356a, 356b, 356c, 356d, 356e, 356f. Each depression may thus connect one of grooves 354a, 354b, 354c, 354d, 354e, 354f to an adjacent groove. Each depression may correspond to a desired bridge in the surface of an expander, such as one of the bridges in the surface of expander 300 (e.g., bridges 320a, 320b, 320c, 320d, 320e, 320f). As such, depressions 370a, 370b, 370c, 370d, 370e, 370f may be arranged in any configuration desired for bridges on an expander, e.g., rows, alternating rows, or staggered formations, as have been described with regard to bridges 320*a*, 320*b*, 320*c*, 320*d*, 320*e*, 320*f* on expander 300 disclosed herein. As such, when an expander is cast on mold 350, removed, and inverted such that the surface formerly in contact with mold 350 forms the outermost surface of the expander, the expander will have the general size and shape of mold 350, and a surface features that are the mirror image of surface features of mold 350, including, e.g., ridges defined by grooves in mold 350, valleys defined by hills on mold 350, and bridges defined by depressions in mold 350.

Mold 350 may comprise a variety of materials, such as metals, metallic alloys, one or more polymers or copolymers, ceramic materials, wood, stone, coral, or any combination thereof. Exemplary metallic materials include, but are not limited to, aluminum and aluminum alloys. Exemplary polymer or co-polymer materials include, but are not limited to, polyoxymethylene (acetal copolymer), such as Delrin® acetal homopolymers produced by DuPont™. Any other polymer/copolymer materials suitable for providing a mold on which to cast a tissue expander according to the present disclosure may be used.

In some embodiments, a mirror image of a desired surface texture, such as a micro-texture or a nano-texture, may be imparted onto the upper surface 352*a* and/or the lower surface 352*b* of the mold 350, so as to impart the desired surface texture on an expander. Various techniques may be used to texturize the upper surface 352*a* and/or lower surface 352*b*. Various systems and methods for texturizing surfaces of implant molds and mandrels are disclosed in U.S. App. No. 62/334,667, filed on May 11, 2016, and U.S. App. No. 62/410,121, filed on Oct. 19, 2016, which are incorporated by reference herein in their entireties. For example, mold 350 may be impacted (e.g., blasted or sandblasted) with an abrasive substance, such as a plurality of abrasive particles. Exemplary materials for the abrasive particles may include, but are not limited to, staurolite minerals, quartz, kyanite, titanium minerals and/or their alloys, zircon, heavy metals (e.g., cadmium, selenium, ferrous iron, and/or steel alloys such as tungsten alloys, chromium alloys, magnesium alloys, molybdenum alloys, and vanadium alloys). In some examples, the abrasive particles may be generally non-spherical in shape, e.g., irregular-shaped particles. For example, the particles may have a granular, irregular shape. In other examples, the abrasive particles may be generally spherical, ovoid, or otherwise regular in shape. In some examples, the abrasive particles may have generally rounded surfaces. In at least one example, the abrasive particles may comprise quartz, and may have generally rounded surfaces clean from extraneous debris, e.g., having less than about 7.0%, less than about 5.0%, less than about 3.0% free silica, or less than about 1.0% free silica.

The composition and shape of the particles may be selected based at least partially on the composition of the mold 350, e.g., to provide for a difference in Mohs hardness between the abrasive particles and the mold 350. In some examples, the abrasive particles may have a Mohs hardness ranging from 5.0 to 8.0, such as from 5.0 to 6.5, from 6.5 to 7.0, or from 7.0 to 8.0. For example, the abrasive particles may have a Mohs hardness that is 1-3 values greater than the material(s) of the mold 350.

The average diameter of the abrasive particles may range from about 10 µm to about 500 µm, such as from about 50 µm to about 450 µm, from about 50 µm to about 250 µm, from about 50 µm to about 100 µm, or from about 75 µm to about 125 µm. In at least one example, the abrasive particles may comprise quartz with an average diameter ranging from about 50 µm to about 100 µm (e.g., a mesh screen size in the range of 50-100 µm).

Abrasive particles may be blasted at the mold surface 352*a*, 352*b* from, for example, a nozzle. The distance between the nozzle and the mold surfaces 352*a*, 352*b* may also be adjusted to affect the surface texture. The distance between the nozzle and the mandrel surface may range from about 2 cm to about 75 cm, such as from about 5 cm to about 50 cm, from about 5 cm to about 25 cm, from about 25 cm to about 50 cm, from about 10 cm to about 35 cm, or from about 10 cm to about 25 cm.

An expander may then be made by, e.g., coating the surface of mold 350 with a material including, e.g., silicone, polyurethane, or a silicone-polyurethane co-polymer. The material may be allowed to set by, e.g., curing. Upon removal of the set material from mold 350, the material may be inverted, such that the portion of the material previously contacting the surface of mold 350 forms the outermost surface of the expander.

Figure 4:
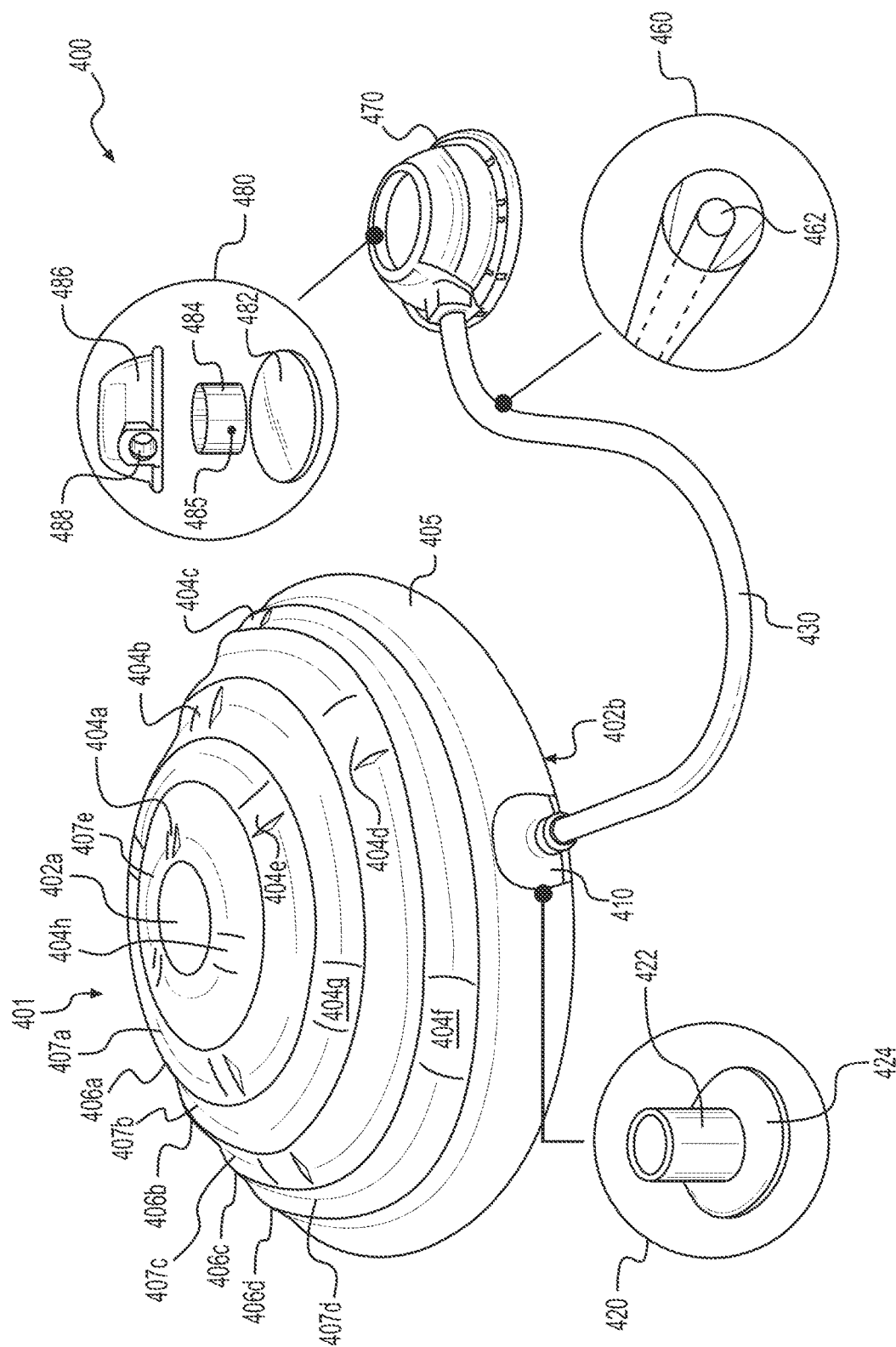
FIG. 4 shows an exemplary system, according to some aspects of the present disclosure.

FIG. 4 (including close-up views 420, 460, and 480) depicts an exemplary tissue expander system 400, including expander 401 and port 470, which are connected by connector tube 430. Expander 401 comprises a shell 405 having an anterior side 402*a* and a posterior side 402*b*. Expander 401 may have a general size and shape similar to, and may include any of the features of, expanders 100, 200, and/or 300—for example, expander 401 may include ridges 406*a*, 406*b*, 406*c*, 406*d* having shapes and configurations similar to ridges 104*a*, 104*b*, 104*c* of expander 100, and valleys 407*a*, 407*b*, 407*c*, 407*d* having shapes and configurations similar to valleys 106*a*, 106*b*, 106*c*, 106*d* of expander 100. Expander assembly 401 may also include a port connection 410 similar to port connection 110. As depicted in close-up view 420, port connection 410 may include both a base 424 and a protrusion 422, which may fluidly connect to, e.g., connector tube 430. Base 424 may be sealed to shell 405, e.g., by vulcanization or glue, or may be molded as a single piece with shell 405.

Bridges, e.g., bridges 404*a*, 404*b*, 404*c*, 404*d*, 404*e*, 404*f*, 404*g*, 404*h* may be circumferentially disposed around anterior side 402*a* of expander 401. Similar to bridges 320*a*, 320*b*, 320*c*, 320*d*, 320*e*, 320*f* of expander 300, each bridge may be a raised section of the shell 405 crossing a valley between two adjacent ridges in the shell. For example, bridge 404*g* may be a raised portion of shell 405 crossing valley 407*b*, between ridges 406*a* and 406*b*. The bridges may be arranged in rows radiating in a direction radially outward from a point on anterior side 402*a*. As with bridges of expander 300, bridges in a single row may cross alternating valleys. Adjacent rows of bridges may radiate outward from anterior side 402*a* at intervals of 60°. Bridges in adjacent rows may cross different alternating valleys; for example, the row of bridges 404*d* and 404*e* may cross valleys 407*c* and 407*a*, respectively, while the adjacent row of bridges 404*f*, 404*g*, and 404*h* may cross valleys 407*d*, 407*b*, and 407*e*, respectively. In further embodiments, the bridges may have any number and/or arrangement, as discussed above in connection to the bridges of expander 300. As with channels 212, 214, 216, 218 and bridges 320*a*, 320*b*, 320*c*, 320*d*, 320*e*, 320*f*, each bridge of expander 401 may have a height across the valley it crosses so as to create a "break" in the valley and connect each of ridges 406*a*, 406*b*, 406*c*, 406*d* to an adjacent ridge. In this manner, fluid introduced into expander 401 may travel between the ridges of expander 401 such that any forces exerted on expander 401 are distributed across the surface of expander 401, promoting even expansion and contraction, and controlling wrinkling of expander 401.

As with bridges 320a, 320b, 320c, 320d, 320e, 320f, bridges on expander 401 may be present in a variety of numbers and configurations. For example, as depicted in FIG. 4, six rows of bridges may radiate outward from anterior side 302a, and the rows may be disposed about anterior side 302a at equal intervals. In further embodiments, two, three, four five, seven, eight, or more rows of bridges may radiate outward on anterior side 302a, at equal or unequal intervals. For example, a first pair of adjacent rows of bridges may be disposed at a 45° angle to one another, and a second pair of adjacent rows of bridges may be disposed at a 135° angle to one another.

In yet further embodiments, each row of bridges may include a bridge crossing every third valley or every fourth valley, as opposed to every other valley. In yet further embodiments, the bridges may not be arranged in rows, but rather may be circumferentially distributed around a point on anterior side 402a in a staggered formation. One of skill in the art will recognize that the bridges may be present in any number, configuration and placement that promotes even flow of fluid inside expander 401 between each of ridges 406a, 406b, 406c, and 406d, without adversely affecting the size and shape of expander 401. As with expanders 200 and 300, one of skill in the art will further understand that the promotion of even flow of fluid inside expander 401 may promote uniform expansion of expander 401 upon introduction of more fluid inside expander 401.

Port 470 may include, as pictured in view 480, a base 482, a ring 484, and a cap 486, each of which may be made using one or more biocompatible materials, such as plastic (e.g., polyoxymethylene), silicone, or metal (e.g., titanium). Port 470 may be fluidly connected to expander 401 and may be configured to receive fluid for delivery into, or removal from, expander 401. Cap 486 may include an insertion point through which fluid may be received into port 470, and an exit hole 488 through which fluid may be fed to expander 401. Cap 486 may be made of, e.g., a self-sealing material that may be penetrated by a fluid delivery device, such as a needle that may deliver fluid. Ring 484 may be located below cap 486 and may surround the insertion point in cap 486. Ring 484 may include, e.g., a material that may resist penetration by a fluid delivery device, such as a metal or plastic material. Ring 484 may have an aperture 485 through which fluid introduced via cap 486 may travel to exit hole 488. Base 482 may also include a material that may resist penetration by a fluid delivery device, such as a metal or plastic material. Base 482 may be affixed to ring 484 and/or cap 486 so as to create an enclosure into which fluid may be delivered through cap 486, and out of which fluid may exit through exit hole 488.

Port 470 may be fluidly connected to expander 401 via, for example, connector tube 430. Connector tube 430 may include a lumen 462 (depicted in view 460) suitable for carrying fluid from port 470 to port connection 410. Connector tube 430 may be made of one or more biocompatible materials suitable for implantation in a patient's body. In some embodiments, connector tube 430 may include any material suitable for inclusion in expander 401. In some embodiments, connector tube 430 may have an inner or outer surface having a texture, such as any texture suitable for an inner or outer surface of expander 401. In some embodiments, connector tube 430 may be flexible, such that it may be bent into multiple configurations. In some embodiments, connector tube 430 may be kink resistant, such that it does not collapse and limit or prevent flow of fluids inside. Connector tube 430 may be any suitable length allowing for a desired placement of expander 401 and port 470. Connector tube 430 may be fluidly connected on one end to port 470 via, for example, exit hole 488, and may be fluidly connected on the other end to an opening into an interior of expander 401, such as port connection 410. In some embodiments, expander system 400 may include one or more valves (not pictured) which may restrict the flow of fluid out of or into expander 401.

In some embodiments, port 470 may be connected directly to expander 401 without connector tube 430. In alternative embodiments, port 470 may be integrated into shell 405 of expander 401. For example, a top of port cap 486 may be approximately flush with a portion of anterior side 402a or posterior side 402b of expander 401. In such embodiments, port 470 may be affixed to shell 405 in an opening in anterior side 402a or posterior side 402b of expander 401.

In some embodiments, port 470 may include one or more features configured to facilitate locating port 470 in cases where port 470 may not be visible, such as when port 470 is implanted internally in a patient. For example, port 470 may include an electromagnetic coil within ring 484 which may be centered around a needle insertion point in cap 486, and which may be detectable using an electromagnetic signal detector, such as a radiofrequency reader. Detection of the electromagnetic coil may facilitate location of the needle insertion point. Additionally or alternatively, in some embodiments, port 470 may include one or more features configured to prevent overinsertion of a needle through cap 486, such as a reinforced base 482. Various systems and methods for assisting in locating ports and preventing needle overinsertion into ports are disclosed in U.S. application Ser. No. 15/427,599, filed on Feb. 8, 2017, which is incorporated by reference herein in its entirety.

Expanders according to the present disclosure (including expanders 100, 200, 300, and 401) may have a variety of shapes and sizes suitable for their use. For example, while expanders 100, 200, 300, and 401 are depicted as having generally circular shapes when viewed from the anterior side (top view) or posterior side (bottom view) (including, for example, a circular posterior side), expanders according to the present disclosure may have, e.g., oval, teardrop, or other shapes for creating a suitable tissue pocket to receive a similarly-shaped implant. Additionally, the "apex" of expanders according to the present disclosure in their expanded forms (having a generally domed or hemispherical shape as viewed from the side) may be centered or may be off-center. The apex refers to the point on either the anterior or posterior side of an expander that is farthest from the opposite (posterior or anterior, respectively) side of the expander in its expanded form, and may be centered on the anterior or posterior side, or alternatively be located at an off-center point. For example, the apex may be positioned between the center point and the outer edge of the anterior surface, so as to more precisely mimic the shape of the implant to be inserted into the pocket formed by the expander and the desired shape of tissue following insertion of the implant. For example, a tissue expander for use in the breast may have a tear-drop shape and/or an apex that is off-center on the anterior side of the expander, so as to more realistically simulate the shape of a human breast. For such a tear-drop shape, the shell may include a series of ridges and valleys centered at the apex (e.g., concentric or otherwise rounded, such as oval or tear drop in shape), similar to those shown in FIGS. 1A-1B, 2A-2B, and 3A-3B.

Tissue expanders according to the present disclosure may be made in a variety of ways.

Figure 5:
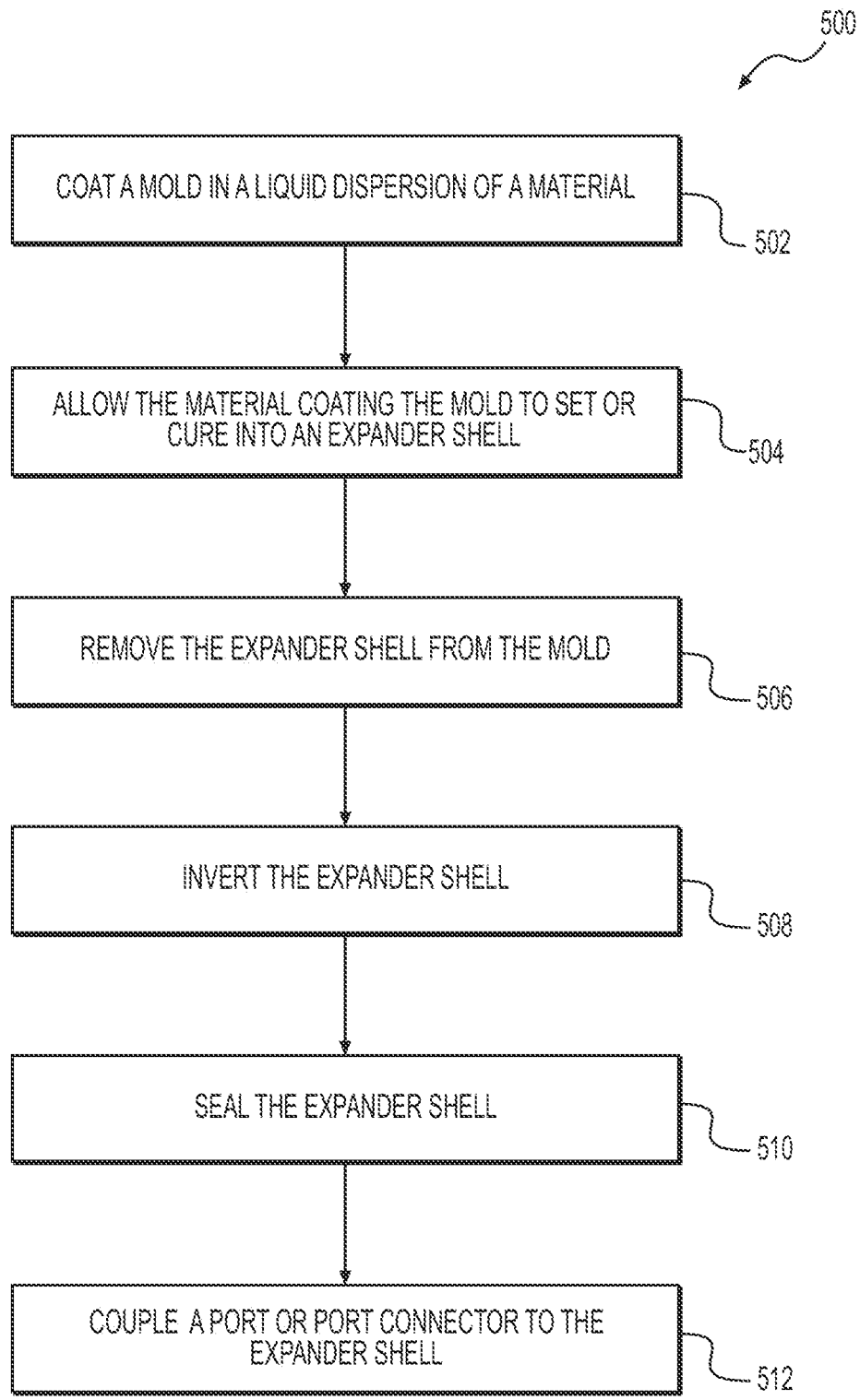
FIG. 5 is a flow diagram showing an exemplary method by which an expander may be made, according to the present disclosure.

FIG. 5 depicts an exemplary method by which an expander according to the present disclosure may be manufactured. According to step 502, a mold may be coated with a liquid dispersion of a biocompatible material. According to step 504, the material coating the mold may be allowed to set or cure (e.g., by application of heat) to form a flexible expander shell. According step 506, the expander shell may be removed from the mold. According to step 508, the expander shell may be inverted, or turned inside out. According to step 510, the expander may be sealed.

According to step 502, a mold may be coated in a liquid dispersion of a material. In some embodiments, the mold may have an inverse of a shape and topography of a desired expander. For example, mold 350 may be used to make an expander such as expander 300. In other embodiments, the mold may have the same shape and topography as a desired expander. In further embodiments, the mold may be a hollow mold, the inside of which may be coated in a liquid dispersion (in which case the shell may not be inverted as discussed below).

The mold may be coated in a dispersion of any material suitable for use in the shell of the desired expander, such as a silicone, a polyurethane, a silicone or polyurethane copolymer, or a silicone and polyurethane copolymer. In some embodiments, the mold may be coated in a dispersion multiple times, so as to create a desired shell thickness. In some embodiments, the mold may be coated in multiple different dispersions, such as dispersions of both clear and colored silicone or other material.

In some embodiments, the mold (such as mold 350) may be coated in a liquid dispersion using a dip-molding process. In other embodiments, a rotational molding process may be used.

According to step 504, the material coating the mold may be allowed to set or cure into an expander shell. In embodiments in which a silicone or polyurethane polymer or co-polymer is used, for example, the material and mold may be cured together at a suitable temperature. For example, a mold coated with a silicone material may be cured at a temperature ranging from about 100° C. to about 200° C., such as from about 125° C. to about 175° C., or from about 125° C. to about 150° C. In some examples, the curing temperature may range from about 125° C. to about 127° C., e.g., about 125° C., about 126° C., or about 127° C. In further examples, the curing temperature may be about 150° C.

According step 506, the expander shell may be removed from the mold. In some embodiments, an aperture may exist or be created in the shell so as to remove the shell from the mold. According to step 508, the expander shell may then be inverted, or turned inside out. Thus, for example, in the case of a dipped mold, the surface of the shell formerly in contact with the mold (e.g., mold 350) may form an exterior surface of the shell having a texture and topography that is a mirror image of the surface of the mold. Alternatively, the cured shell may be removed from a mold, such as a rotational mold, and may not be turned inside out.

According to step 510, the expander shell may be sealed. For example, if an aperture existed or was created so as to remove the expander shell from the mold, such an aperture may be sealed using, e.g., vulcanization, glue, or other methods. In some examples, the expander shell may be sealed to a port or a port connector, through which fluid may be introduced into the expander. For example, the port or port connector may be coupled to, or incorporated into, the aperture of the shell used to remove the mold, or another aperture or opening created so as to accommodate the port or port connector. In some embodiments, a connector tube may be coupled to a port connector that is coupled to or otherwise incorporated into an aperture of the shell, and may be affixed using, e.g., vulcanization or glue. In further embodiments, a port or port connector connector may be removably coupled to a connector tube. The above-described process is exemplary in nature. Steps of this process may be performed in a different order, or removed altogether. In further embodiments, expanders according to the present disclosure may be made according to any way that is known to those of ordinary skill in the art.

Expanders according to the present disclosure may be used in a variety of different procedures. For example, expanders according to the present disclosure may be useful in tissue reconstruction surgery and/or elective surgery for esthetic purposes, including minimally-invasive surgery. For example, the expanders of the present disclosure may include a flexible, elastic shell that allows the expanders to be folded or rolled prior to insertion into patient tissue, thus allowing them to be inserted through a relatively small incision. The elasticity and/or surface features of the expanders disclosed herein may allow the expanders to roll and unroll, fold and unfold, and/or expand and contract in a controlled, predictable fashion, thus allowing for control and predictability of the expanders' behavior upon implantation in a patient. Additionally, the topographies of expanders disclosed herein may provide a structure and/or shape to which the expanders may return more easily, thus helping to avoid unwanted wrinkling or creasing of the expanders. The expanders may be inserted into a patient without fluid (e.g., to be filled after insertion) or partially filled with fluid (e.g., to be additionally filled after insertion).

Figure 6A:
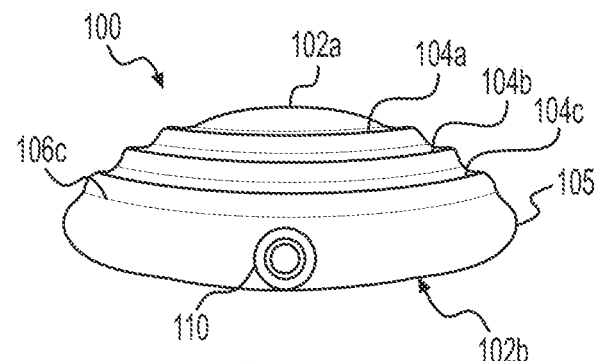
FIGS. 6A, 6B, and 6C show three states of expansion of the exemplary device of FIGS. 1A and 1B.
Figure 6B:
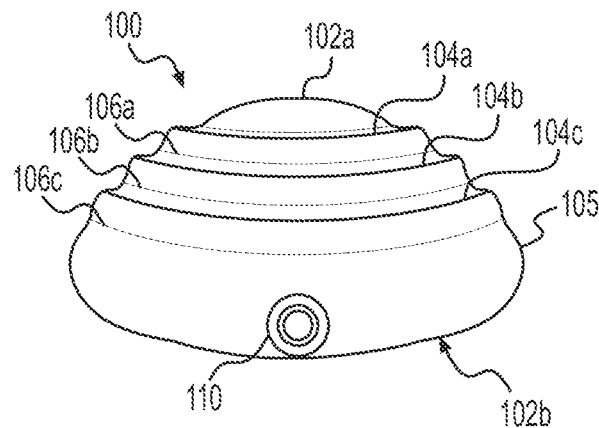
Figure 6C:
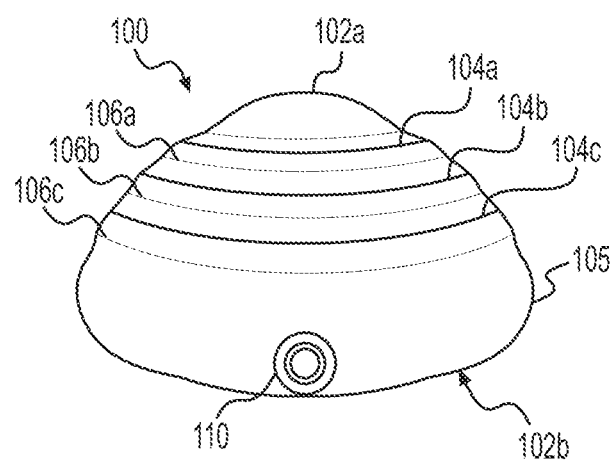

As has been previously discussed herein, expanders according to the present disclosure (such as expanders 100, 200, 300, and 401) may expand uniformly to several different sizes. This is depicted with regard to expander 100 in FIGS. 6A-6C. FIG. 6A depicts, for example, expander 100 in a contracted form. For example, expander 100 may be inserted into a patient while in the contracted form. FIG. 6B depicts, for example, expander 100 in a partially expanded form, such as when some fluid has been introduced into expander 100, e.g., following insertion into the patient. FIG. 6C depicts, for example, expander 100 in more fully expanded form, when additional fluid has been introduced into expander 100, e.g., after the expander 100 has been implanted for a period of time to allow for gradual tissue expansion. As mentioned above, any suitable fluid may be used, including, but not limited to, water, saline solution (or other biocompatible solution), silicone gel (or other biocompatible gel), or air (or other biocompatible gas, e.g., nitrogen). Tissue expansion may occur over the span of weeks to months, e.g., from about 4 weeks to about 24 weeks, or from about 6 weeks to about 8 weeks, e.g., about 4, 6, 8, 10, 12, 14, 16, 20, 22, or 24 weeks or more. The fluid may be at least partially or completely removed from expander 100, e.g., via port connector 110, prior to removal from the patient once sufficient tissue expansion has been achieved.

Any aspect or feature in any embodiment may be used with any other embodiment set forth herein. It will be apparent to those skilled in the art that various modifications and variations can be made in the disclosed implants, implant features, and processes without departing from the scope of the disclosure. Other embodiments will be apparent to those skilled in the art from consideration of the specification and practice of the disclosure disclosed herein. It is intended that the specification and examples be considered as exemplary only. Other aspects and embodiments of the present disclosure will be apparent to those skilled in the art from consideration of the specification and practice of the embodiments disclosed herein.

What is claimed is:

1. A tissue expander comprising:
a flexible shell defining a cavity configured to receive a fluid therein and to expand and contract upon introduction and removal, respectively, of the fluid into the cavity, the shell including a posterior side and an anterior side having an apex,
wherein the anterior side includes a plurality of ridges disposed circumferentially about the apex, the plurality of ridges including two channels connecting two adjacent ridges, wherein the two channels each extend radially outward and are disposed at least 45° apart about a circumference of the shell, and wherein each ridge curves in an arc about the apex to define a length from a first end of the ridge to a second end of the ridge, each ridge having a width shorter than the length of each respective ridge.

2. The tissue expander of claim 1, wherein the plurality of ridges includes a first annular ridge that has a uniform height along its entire length and a second annular ridge concentric with the first annular ridge.

3. The tissue expander of claim 1, wherein the plurality of ridges includes at least three ridges each separated from an adjacent ridge by a valley, the anterior side further comprising:
a first channel connecting a first ridge of the at least three ridges to a second ridge of the at least three ridges, and traversing a valley between the first ridge and the second ridge; and
a second channel connecting the second ridge to a third ridge of the at least three ridges, and traversing a valley between the second ridge and the third ridge;
wherein the first channel, the second channel, and the apex are not co-linear.

4. The tissue expander of claim 3, wherein the first channel does not connect to the third ridge.

5. The tissue expander of claim 1, wherein the shell is flexible and comprises silicone, polyurethane, or a copolymer thereof.

6. The tissue expander of claim 1, wherein the shell has a uniform thickness ranging from about 0.3 mm to about 1.1 mm.

7. The tissue expander of claim 1, wherein at least one of the anterior side or the posterior side of the shell is textured.

8. The tissue expander of claim 1, wherein the shell has a cross-sectional area that decreases from the posterior side to the anterior side providing the tissue expander with an arched shape upon expansion.

9. The tissue expander of claim 1, wherein the posterior side does not include ridges.

10. The tissue expander of claim 1, wherein the anterior side includes a port or port connection, the port or port connection being farther away from the apex than each ridge of the plurality of ridges.

11. A tissue expander, comprising:
a flexible shell defining a cavity configured to receive a fluid therein and to expand and contract upon introduction and removal, respectively, of the fluid into the cavity, the shell including:
a plurality of ridges, each ridge having a uniform height and curving along a surface of the shell in an arc around an apex to define a first end of the ridge to a second end of the ridge, and each ridge having a width shorter than the length of the respective ridge; and
two channels from a plurality of channels connecting two adjacent ridges, wherein the two channels each extend radially outward and are disposed at least 45° apart about a circumference of the shell;
wherein the shell has a uniform thickness.

12. The tissue expander of claim 11, wherein the plurality of ridges includes at least three concentric ridges.

13. The tissue expander of claim 11, further comprising a port integrated into the shell.

14. The tissue expander of claim 11, wherein the plurality of channels are disposed in a staggered configuration.

15. The tissue expander of claim 11, wherein the tissue expander has a circular, oval, or teardrop cross-sectional shape.

16. A tissue expander comprising:
a flexible shell defining a cavity configured to receive a fluid therein and to expand and contract upon introduction and removal, respectively, of the fluid into the cavity, the shell including a posterior side and an anterior side having an apex,
wherein the anterior side includes a plurality of ridges disposed circumferentially about the apex, the plurality of ridges including two channels connecting two adjacent ridges, wherein the two channels each extend radially outward and are disposed at least 45° apart about a circumference of the shell, and wherein each ridge curves about the apex to define an arc length from a first end of the ridge to a second end of the ridge, each ridge having a width shorter than the arc length of each respective ridge; and
wherein the anterior side includes a port integrated into the shell.

17. The tissue expander of claim 16, wherein the port is detectable when implanted internally in a patient by using an electromagnetic signal detector external to the patient.

* * * * *

UNITED STATES PATENT AND TRADEMARK OFFICE
CERTIFICATE OF CORRECTION

| | | |
|---|---|---|
| PATENT NO. | : 11,571,271 B2 | Page 1 of 1 |
| APPLICATION NO. | : 16/345261 | |
| DATED | : February 7, 2023 | |
| INVENTOR(S) | : Martinez et al. | |

It is certified that error appears in the above-identified patent and that said Letters Patent is hereby corrected as shown below:

On the Title Page

On page 3, in Column 1, under "Foreign Patent Documents", Line 1, delete "10984321" and insert --109843210-- therefor On page 3, in Column 2, under "Other Publications", Line 25, delete "10-2019-7012393,Response" and insert --10-2019-7012393, Response-- therefor On page 3, in Column 2, under "Other Publications", Line 26, before "Preliminary", insert --to Notice of--

Signed and Sealed this
Thirteenth Day of February, 2024

Katherine Kelly Vidal
*Director of the United States Patent and Trademark Office*